United States Patent
Thomas et al.

(10) Patent No.: US 11,186,539 B2
(45) Date of Patent: Nov. 30, 2021

(54) PROCESS FOR SYNTHESIS AND PURIFICATION OF (2R,6R)-HYDROXYNORKETAMINE

(71) Applicant: THE UNITED STATES OF AMERICA, AS REPRESENTED BY THE SECRETARY, DEPARTMENT OF HEALTH AND HUMAN SERVICES, Bethesda, MD (US)

(72) Inventors: Craig J. Thomas, Gaithersburg, MD (US); Patrick Joseph Morris, Laurel, MD (US); Richard Andrew Castledine, Northumberland (GB); Samuel Lawrence Bourne, Northumberland (GB)

(73) Assignee: THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 0 days.

(21) Appl. No.: 15/734,710

(22) PCT Filed: Jun. 4, 2019

(86) PCT No.: PCT/US2019/035360
§ 371 (c)(1),
(2) Date: Dec. 3, 2020

(87) PCT Pub. No.: WO2019/236557
PCT Pub. Date: Dec. 12, 2019

(65) Prior Publication Data
US 2021/0246099 A1 Aug. 12, 2021

Related U.S. Application Data

(60) Provisional application No. 62/680,183, filed on Jun. 4, 2018.

(51) Int. Cl.
| C07C 221/00 | (2006.01) |
| C07C 249/02 | (2006.01) |
| C07F 7/18 | (2006.01) |
| C07C 269/04 | (2006.01) |

(52) U.S. Cl.
CPC .......... *C07C 221/00* (2013.01); *C07C 249/02* (2013.01); *C07C 269/04* (2013.01); *C07F 7/188* (2013.01); *C07B 2200/13* (2013.01)

(58) Field of Classification Search
None
See application file for complete search history.

(56) References Cited

U.S. PATENT DOCUMENTS

2019/0135732 A1* 5/2019 Thomas ................ C07C 221/00

FOREIGN PATENT DOCUMENTS

| WO | 2014057414 A1 | 4/2014 |
| WO | 2017165878 A1 | 9/2017 |

OTHER PUBLICATIONS

International Search Report issued in Application No. PCT/US2019/035360 dated Aug. 16, 2019, 5 pages.
Written Opinion issued in Application No. PCT/US2019/035360 dated Aug. 16, 2019, 7 pages.
Zanos, Panos et al., "NMDAR inhibition-independent antidepressant actions of ketamine metabolites", Nature, May 26, 2016, vol. 533; 62 pages.

* cited by examiner

*Primary Examiner* — Sudhakar Katakam
*Assistant Examiner* — Jennifer C Sawyer
(74) *Attorney, Agent, or Firm* — Cantor Colburn LLP

(57) ABSTRACT

A process for the preparation of (2R,6R)-hydroxynorketamine is provided. The process requires no chromatography purification and affords the (2R,6R)-hydroxynorketamine in eight steps with a 26% overall yield and greater than 97% purity.

19 Claims, No Drawings

PROCESS FOR SYNTHESIS AND PURIFICATION OF (2R,6R)-HYDROXYNORKETAMINE

CROSS-REFERENCE TO RELATED APPLICATION

This application is a § 371 US National Stage application of International Application No. PCT/US2019/035360 filed 4 Jun. 2019, and claims priority to U.S. Provisional Patent Application No. 62/680,183 filed 4 Jun. 2018. Each of these applications are incorporated herein by reference in their entireties.

BACKGROUND OF THE INVENTION

Field of Invention

The present invention is directed to a synthesis of a therapeutic agent for curing treatment-resistant depression, and more specifically, to an improved process for synthesis and purification of (2R,6R)-hydroxynorketamine.

Brief Description of Related Art

Depression is a mood disorder affecting millions of people worldwide, which is characterized by a persistent feeling of sadness and loss of interest. Depression is caused by a combination of biological, psychological, and social sources of distress, which results in changes in brain function, including altered activity of certain neural circuits in the brain. Various therapeutic agents, known as antidepressants, have been proposed and developed to treat depression. However, as many as two-thirds of people with the disease are not helped with the first antidepressant they try.

Recently, (2R,6R)-hydroxynorketamine was discovered as a leading compound for curing treatment-resistant depression. The compound exerted rapid onset and was shown to have behavioral, electroencephalographic, electrophysiological, and cellular antidepressant-related actions in mice. Importantly, (2R,6R)-hydroxynorketamine was found to be free of undesired central nervous system (CNS) characteristics, such as anesthetic properties and abuse potential, frequently associated with other ketamines.

The existing published route to (2R,6R)-hydroxynorketamine, however, provided the target product in only 2.8% overall yield over 8 steps. Therefore, there remains a need for an efficient and cost-effective synthesis to produce large amounts of (2R,6R)-hydroxynorketamine in high yield.

SUMMARY OF THE INVENTION

In an embodiment, a process for the preparation of (2R,6R)-hydroxynorketamine is provided. The process includes the steps of: applying thermal flow conditions to a compound

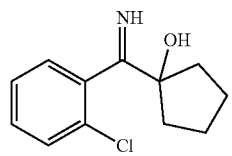 [SMILES: N=C(c1ccccc1Cl)C1(O)CCCC1]

to obtain a compound

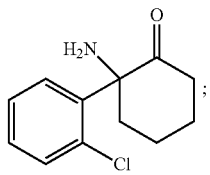 [SMILES: NC1(c2ccccc2Cl)CCCCC1=O]

and converting the compound

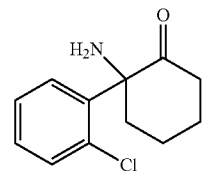 [SMILES: NC1(c2ccccc2Cl)CCCCC1=O]

to (2R,6R)-hydroxynorketamine hydrochloride.

The step of converting the compound

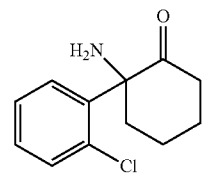 [SMILES: NC1(c2ccccc2Cl)CCCCC1=O]

to (2R,6R)-hydroxynorketamine hydrochloride may further include contacting the compound

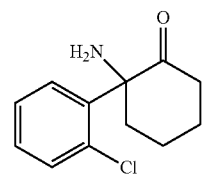 [SMILES: NC1(c2ccccc2Cl)CCCCC1=O]

with the optically active isomer of pyroglutamic acid to obtain an adduct of the compound

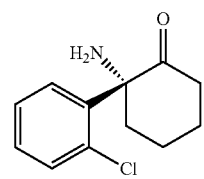 [SMILES: N[C@@]1(c2ccccc2Cl)CCCCC1=O]

and the optically active isomer of pyroglutamic acid.

The step of applying thermal flow conditions to the compound

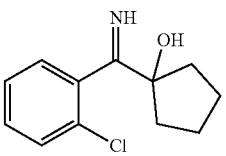 [SMILES: N=C(c1ccccc1Cl)C1(O)CCCC1]

to obtain a compound

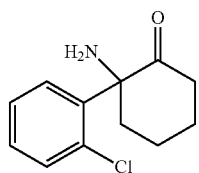 [SMILES: NC1(c2ccccc2Cl)CCCCC1=O]

may be carried out by passing the compound

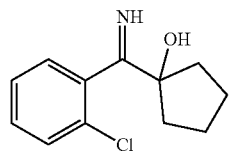 [SMILES: N=C(c1ccccc1Cl)C1(O)CCCC1]

through a thermal flow reactor at a temperature of about 120° C. about 220° C. with a retention time of about 5 minutes to about 2 hours.

The step of contacting the compound

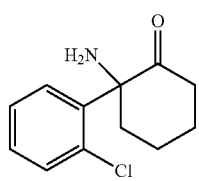 [SMILES: NC1(c2ccccc2Cl)CCCCC1=O]

with the optically active isomer of pyroglutamic acid to obtain the adduct of the compound

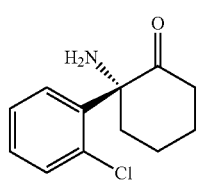 [SMILES: N[C@@]1(c2ccccc2Cl)CCCCC1=O]

and the optically active isomer of pyroglutamic acid may include:
(i) contacting the compound

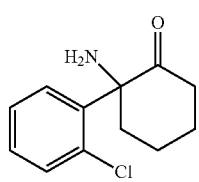 [SMILES: NC1(c2ccccc2Cl)CCCCC1=O]

with the optically active isomer of pyroglutamic acid to obtain the adduct of the compound

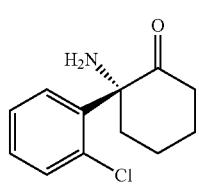

and the optically active isomer of pyroglutamic acid and its enantiomer; and separating the adduct of the compound

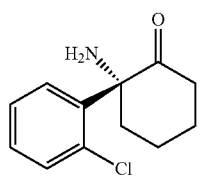 [SMILES: N[C@@]1(c2ccccc2Cl)CCCCC1=O]

and the optically active isomer of pyroglutamic acid from its enantiomer.

The step of separating the adduct of the compound

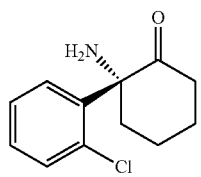 [SMILES: N[C@@]1(c2ccccc2Cl)CCCCC1=O]

and the optically active isomer of pyroglutamic acid from its enantiomer may take place by crystallization.

The step of converting the adduct of the compound

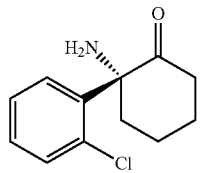 [SMILES: N[C@@]1(c2ccccc2Cl)CCCCC1=O]

and the optically active isomer of pyroglutamic acid to (2R,6R)-hydroxynorketamine hydrochloride may include the step of:

reacting the adduct of the compound

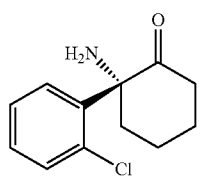 [SMILES: N[C@@]1(c2ccccc2Cl)CCCCC1=O]

and the optically active isomer of pyroglutamic acid with a Boc-protecting group-containing agent to obtain a compound

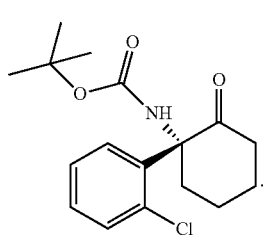 [SMILES: CC(C)(C)OC(=O)N[C@@]1(c2ccccc2Cl)CCCCC1=O]

The Boc-protecting group-containing agent may be di-tert-butyl dicarbonate.

The step of reacting the adduct of the compound

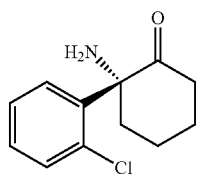 [SMILES: N[C@@]1(c2ccccc2Cl)CCCCC1=O]

and the optically active isomer of pyroglutamic acid with a Boc-protecting group-containing agent to obtain a compound

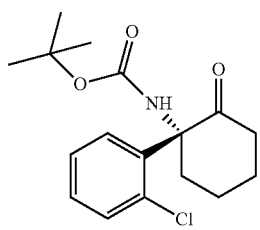 [SMILES: CC(C)(C)OC(=O)N[C@@]1(c2ccccc2Cl)CCCCC1=O]

may be followed by the steps of:

contacting the compound

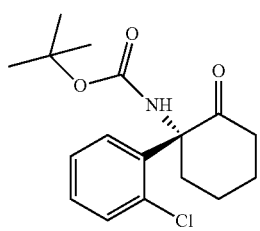 [SMILES: CC(C)(C)OC(=O)N[C@@]1(c2ccccc2Cl)CCCCC1=O]

with a base and trimethylsilyl chloride to obtain a compound

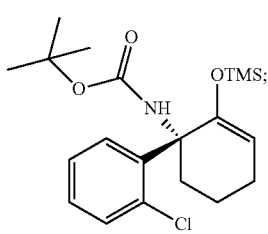

and contacting the compound

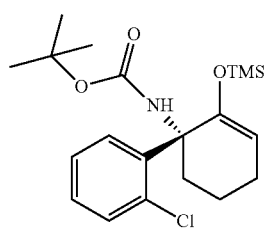

with an oxidizing agent followed by hydrochloric acid to obtain a compound

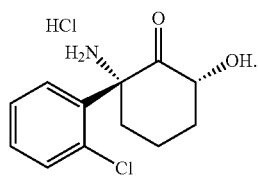 [SMILES: N[C@@]1(c2ccccc2Cl)CCC[C@@H](O)C1=O ; Cl]

The oxidizing agent is meta-chloroperoxybenzoic acid.

The compound

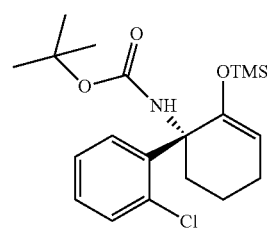

may be contacted with meta-chloroperoxybenzoic acid at about −40° C. in toluene as a solvent to provide an intermediate adduct, and the intermediate adduct may be contacted with hydrochloric acid to provide the compound

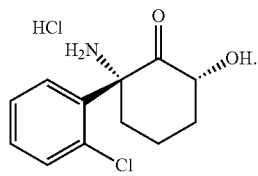 [SMILES: N[C@@]1(c2ccccc2Cl)CCC[C@@H](O)C1=O ; Cl]

The step of contacting the compound

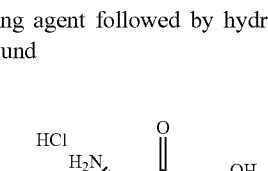

with an oxidizing agent followed by hydrochloric acid to obtain a compound

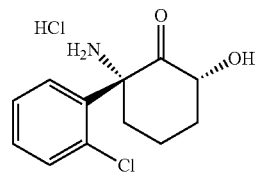 [SMILES: N[C@@]1(c2ccccc2Cl)CCC[C@@H](O)C1=O ; Cl]

is followed by the step of:
 purifying the compound

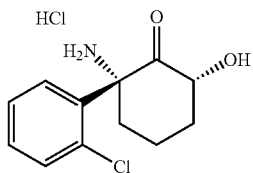 [SMILES: N[C@@]1(c2ccccc2Cl)CCC[C@@H](O)C1=O ; Cl]

to obtain (2R,6R)-hydroxynorketamine hydrochloride.

The purification may take place by recrystallization from a solvent. The recrystallization solvent may include acetone, water, ethanol, ethyl acetate, or any combination thereof.

The recrystallization solvent may be a mixture comprising acetone and water. A ratio of acetone to water in the mixture may be from 10:1 to 500:1, for example, 20:1.

The optically active isomer of pyroglutamic acid may be (L)-pyroglutamic acid, and the adduct of the compound

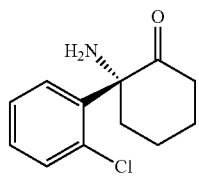 [SMILES: N[C@@]1(c2ccccc2Cl)CCCCC1=O]

and the (L)-pyroglutamic acid may be separated in a yield of 98% or greater and enantiomeric purity of 97% or greater.

The purity of the (2R,6R)-hydroxynorketamine hydrochloride may be 97% or greater.

The step of applying thermal flow conditions to the compound

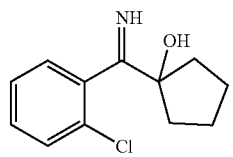 [SMILES: N=C(c1ccccc1Cl)C1(O)CCCC1]

to obtain a compound

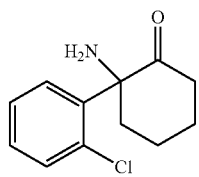 [SMILES: NC1(c2ccccc2Cl)CCCCC1=O]

may be preceded by the step of:
 reacting the compound

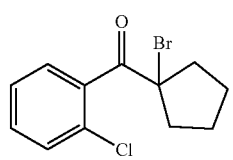 [SMILES: O=C(c1ccccc1Cl)C1(Br)CCCC1]

with an ammonia source to obtain a compound

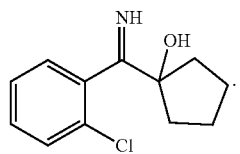 [SMILES: N=C(c1ccccc1Cl)C1(O)CCCC1]

The ammonia source is liquid ammonia.

The step of reacting the compound

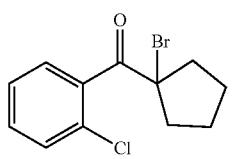 [SMILES: O=C(c1ccccc1Cl)C1(Br)CCCC1]

with an ammonia source to obtain a compound

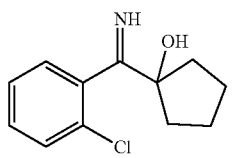 [SMILES: N=C(c1ccccc1Cl)C1(O)CCCC1]

is preceded by the step of:
 reacting a compound

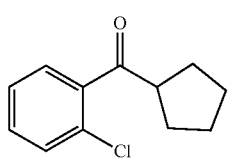 [SMILES: O=C(c1ccccc1Cl)C1CCCC1]

with a brominating source to obtain a compound

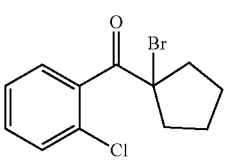

The brominating source is molecular bromine.

In another embodiment, the process for the preparation of (2R,6R)-hydroxynorketamine includes:

Step (a): reacting a compound

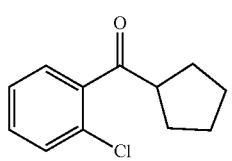 [SMILES: O=C(c1ccccc1Cl)C1CCCC1]

with a brominating source to obtain a compound

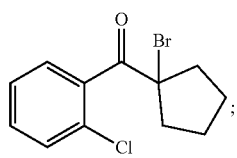 [SMILES: O=C(c1ccccc1Cl)C1(Br)CCCC1]

Step (b): reacting the compound

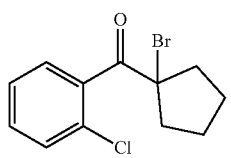 [SMILES: O=C(c1ccccc1Cl)C1(Br)CCCC1]

with an ammonia source to obtain a compound

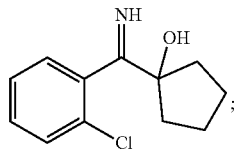 [SMILES: N=C(c1ccccc1Cl)C1(O)CCCC1]

Step (c): applying thermal flow conditions to the compound

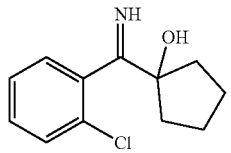 [SMILES: N=C(c1ccccc1Cl)C1(O)CCCC1]

to obtain a compound

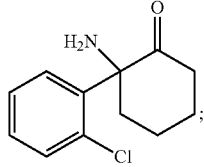 [SMILES: NC1(c2ccccc2Cl)CCCCC1=O]

Step (d): contacting the compound

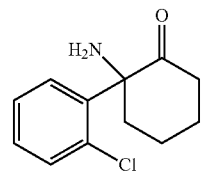 [SMILES: NC1(c2ccccc2Cl)CCCCC1=O]

with an optically active isomer of pyroglutamic acid to obtain an adduct of a compound

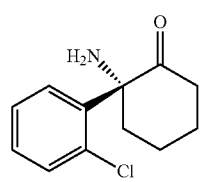 [SMILES: N[C@@]1(c2ccccc2Cl)CCCCC1=O]

and an optically active isomer of pyroglutamic acid and its enantiomer;

Step (e): reacting the adduct of the compound

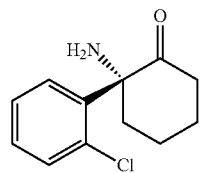 [SMILES: N[C@@]1(c2ccccc2Cl)CCCCC1=O]

and the optically active isomer of pyroglutamic acid with a Boc-protecting group-containing agent to obtain a compound

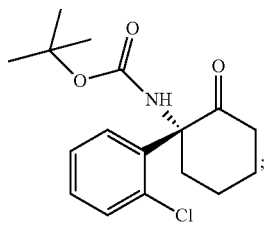 [SMILES: CC(C)(C)OC(=O)N[C@@]1(c2ccccc2Cl)CCCCC1=O]

Step (f): contacting the compound

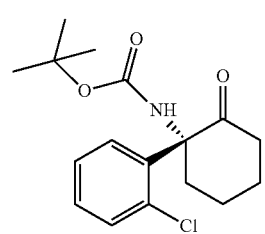 [SMILES: CC(C)(C)OC(=O)N[C@@]1(c2ccccc2Cl)CCCCC1=O]

with a base and trimethylsilyl chloride to obtain a compound

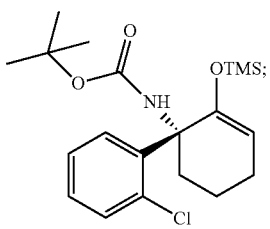

Step (g): contacting the compound

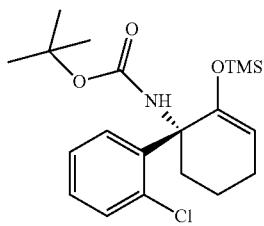

with an oxidizing agent followed by hydrochloric acid to obtain a compound

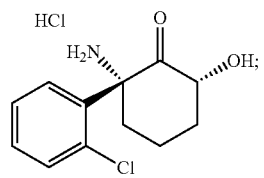 [SMILES: N[C@@]1(c2ccccc2Cl)CCC[C@@H](O)C1=O ; Cl]

and

Step (h): recrystallizing the compound

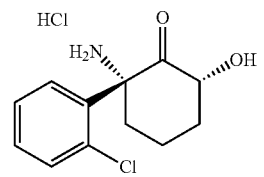 [SMILES: N[C@@]1(c2ccccc2Cl)CCC[C@@H](O)C1=O ; Cl]

to obtain (2R,6R)-hydroxynorketamine hydrochloride.

DETAILED DESCRIPTION

Reference will now be made in detail to embodiments, which may have different forms and should not be construed as being limited to the descriptions set forth herein. Accordingly, the embodiments are merely described below to explain aspects of the present description. As used herein, the term "and/or" includes any and all combinations of one or more of the associated listed items.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The existing sequence for the synthesis of (2R,6R)-hydroxynorketamine, as published in the literature (Zanos et al., Nature, 2016, 533, 481-486) is shown in Scheme 1. This reaction sequence provided the final product with only a 2.8% overall yield in 8 steps. Several procedures in the reaction sequence are not desirable for process scale synthesis. For example, the high temperature thermal rearrangement of β-hydroxyimine 3 to α-aminoketone 4 utilized a microwave reactor and high pressures. In addition, the existing chiral resolution of 4 to 5 was low yielding, and used high volumes of the solvent. Further, the Rubottom oxidation sequence for conversion of Boc-protected α-aminoketone 6 to α-hydroxyketone 8 utilized cryogenic conditions and silica gel column chromatography to purify the products.

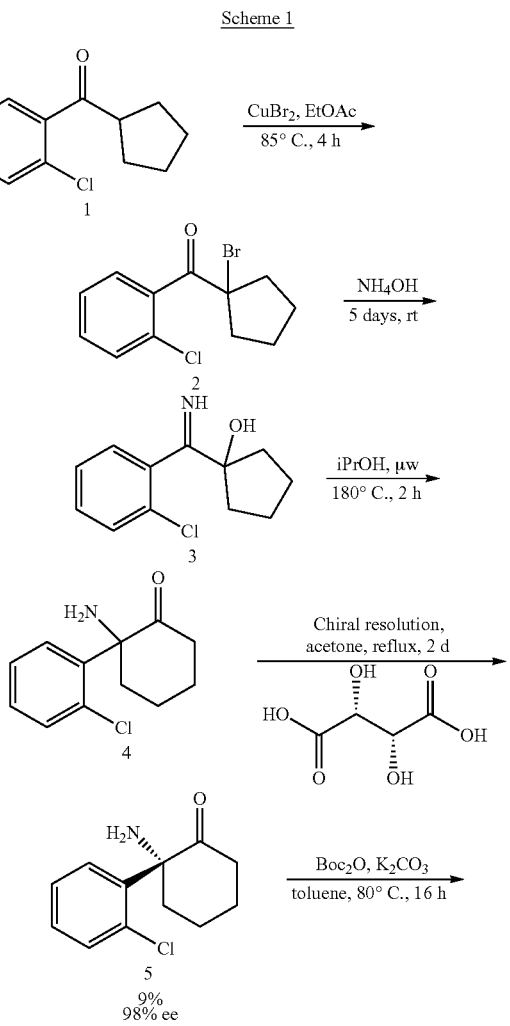

Scheme 1

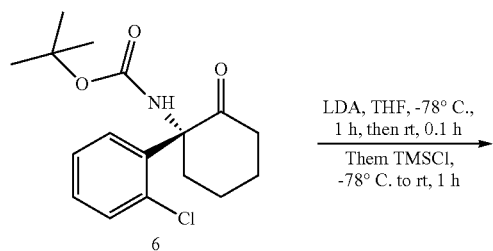

LDA, THF, -78° C.,
1 h, then rt, 0.1 h
Then TMSCl,
-78° C. to rt, 1 h

6

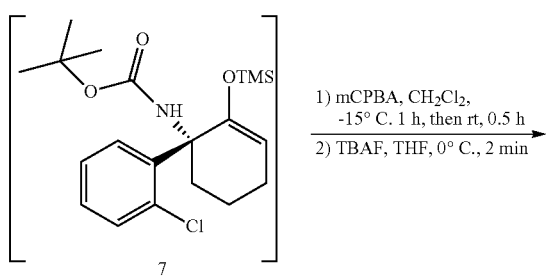

1) mCPBA, CH$_2$Cl$_2$,
-15° C. 1 h, then rt, 0.5 h
2) TBAF, THF, 0° C., 2 min

7

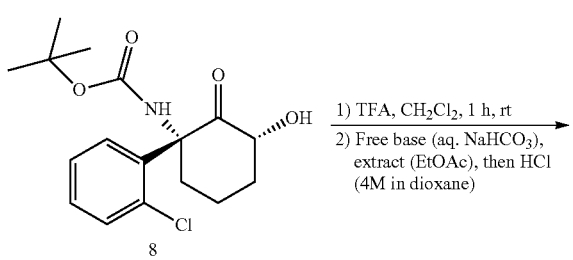

1) TFA, CH$_2$Cl$_2$, 1 h, rt
2) Free base (aq. NaHCO$_3$),
extract (EtOAc), then HCl
(4M in dioxane)

8

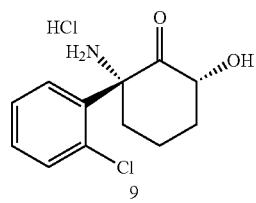

9

The inventors of the present invention discovered a new reaction scheme which resulted in substantial improvement of the published approach to (2R,6R)-hydroxynorketamine. While the intermediates in the new scheme remain the same, the conditions and reagents for each step throughout the process chemistry development process have been significantly changed. The new process results in the overall improvement of the (2R,6R)-hydroxynorketamine yield, eliminates tedious and costly silica gel chromatography purifications, and provides significant cost savings when the process is performed on a large scale.

In an embodiment, a process for the preparation of (2R,6R)-hydroxynorketamine is provided. The process includes the steps of:

applying thermal flow conditions to a compound

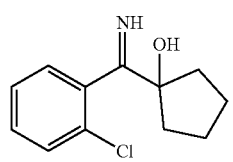 [SMILES: N=C(c1ccccc1Cl)C1(O)CCCC1]

to obtain a compound; and converting the compound

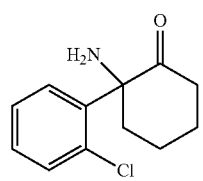 [SMILES: NC1(c2ccccc2Cl)CCCCC1=O]

to (2R,6R)-hydroxynorketamine hydrochloride.

The step of converting the compound

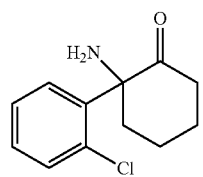 [SMILES: NC1(c2ccccc2Cl)CCCCC1=O]

to (2R,6R)-hydroxynorketamine hydrochloride may further include contacting the compound

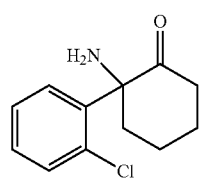 [SMILES: NC1(c2ccccc2Cl)CCCCC1=O]

with the optically active isomer of pyroglutamic acid to obtain an adduct of the compound

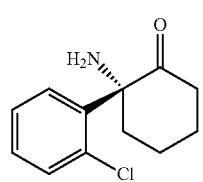 [SMILES: N[C@@]1(c2ccccc2Cl)CCCCC1=O]

and the optically active isomer of pyroglutamic acid.

The step of applying thermal flow conditions to the compound

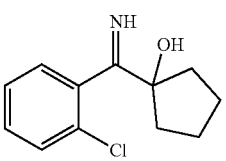 [SMILES: N=C(c1ccccc1Cl)C1(O)CCCC1]

to obtain a compound

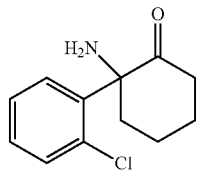 [SMILES: NC1(c2ccccc2Cl)CCCCC1=O]

may be carried out by passing the compound

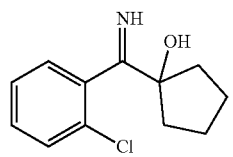 [SMILES: N=C(c1ccccc1Cl)C1(O)CCCC1]

through a thermal flow reactor at a temperature of about 120° C. about 220° C. with a retention time of about 5 minutes to about 2 hours.

The step of contacting

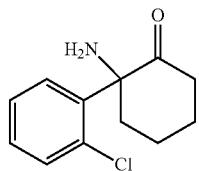 [SMILES: NC1(c2ccccc2Cl)CCCCC1=O]

the compound with the optically active isomer of pyroglutamic acid to obtain the adduct of the compound

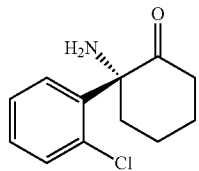 [SMILES: N[C@@]1(c2ccccc2Cl)CCCCC1=O]

and the optically active isomer of pyroglutamic acid may include:

(ii) contacting the compound

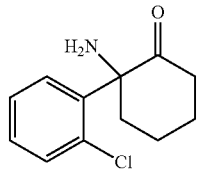 [SMILES: NC1(c2ccccc2Cl)CCCCC1=O]

with the optically active isomer of pyroglutamic acid to obtain the adduct of the compound

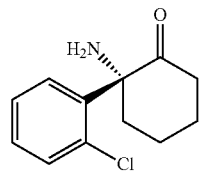 [SMILES: N[C@@]1(c2ccccc2Cl)CCCCC1=O]

and the optically active isomer of pyroglutamic acid and its enantiomer; and separating the adduct of the compound

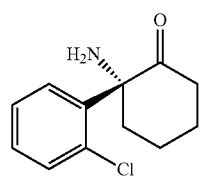 [SMILES: N[C@@]1(c2ccccc2Cl)CCCCC1=O]

and the optically active isomer of pyroglutamic acid from its enantiomer.

The step of separating the adduct of the compound

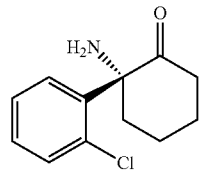 [SMILES: N[C@@]1(c2ccccc2Cl)CCCCC1=O]

and the optically active isomer of pyroglutamic acid from its enantiomer may take place by crystallization.

The step of converting the adduct of the compound

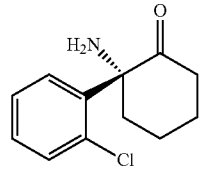 [SMILES: N[C@@]1(c2ccccc2Cl)CCCCC1=O]

and the optically active isomer of pyroglutamic acid to (2R,6R)-hydroxynorketamine hydrochloride may include the step of:

reacting the adduct of the compound

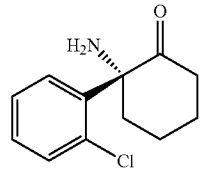 [SMILES: N[C@@]1(c2ccccc2Cl)CCCCC1=O]

and the optically active isomer of pyroglutamic acid with a Boc-protecting group-containing agent to obtain a compound

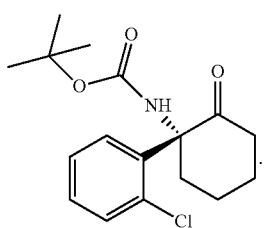 [SMILES: CC(C)(C)OC(=O)N[C@@]1(c2ccccc2Cl)CCCCC1=O]

The Boc-protecting group-containing agent may be di-tert-butyl dicarbonate.

The step of reacting the adduct of the compound

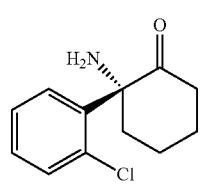 [SMILES: N[C@@]1(c2ccccc2Cl)CCCCC1=O]

and the optically active isomer of pyroglutamic acid with a Boc-protecting group-containing agent to obtain a compound

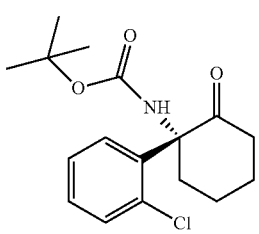 [SMILES: CC(C)(C)OC(=O)N[C@@]1(c2ccccc2Cl)CCCCC1=O]

may be followed by the steps of:
contacting the compound

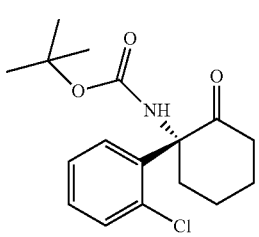 [SMILES: CC(C)(C)OC(=O)N[C@@]1(c2ccccc2Cl)CCCCC1=O]

with a base and trimethylsilyl chloride to obtain a compound

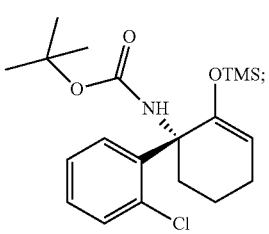

and contacting the compound

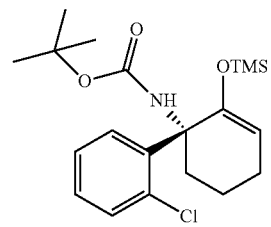

with an oxidizing agent followed by hydrochloric acid to obtain a compound

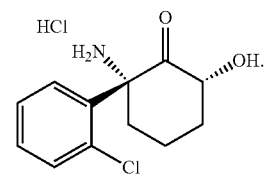 [SMILES: N[C@@]1(c2ccccc2Cl)CCC[C@@H](O)C1=O ; Cl]

The oxidizing agent is meta-chloroperoxybenzoic acid.
The compound

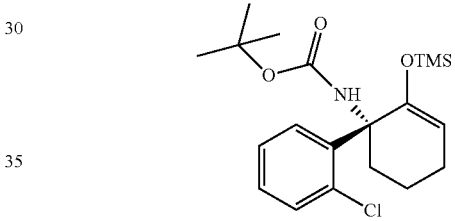

may be contacted with meta-chloroperoxybenzoic acid at about −40° C. in toluene as a solvent to provide an intermediate adduct, and the intermediate adduct may be contacted with hydrochloric acid to provide the compound

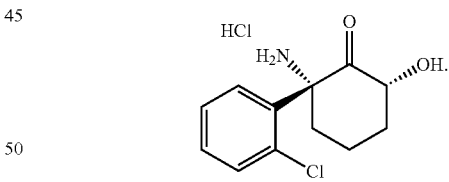

The step of contacting the compound

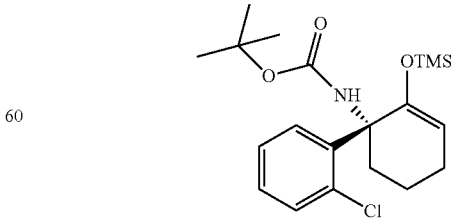

with an oxidizing agent followed by hydrochloric acid to obtain a compound

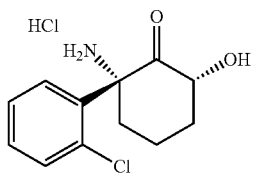 [SMILES: N[C@@]1(c2ccccc2Cl)CCC[C@@H](O)C1=O ; Cl]

is followed by the step of:

purifying the compound

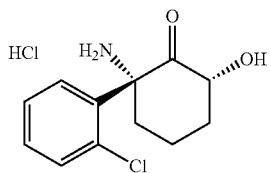 [SMILES: Cl ; N[C@@]1(c2ccccc2Cl)CCC[C@@H](O)C1=O]

to obtain (2R,6R)-hydroxynorketamine hydrochloride.

The purification may take place by recrystallization from a solvent. The recrystallization solvent may include acetone, water, ethanol, ethyl acetate, or any combination thereof.

The recrystallization solvent may be a mixture comprising acetone and water. A ratio of acetone to water in the mixture may be from 10:1 to 500:1, for example, 20:1.

The optically active isomer of pyroglutamic acid may be (L)-pyroglutamic acid, and the adduct of the compound

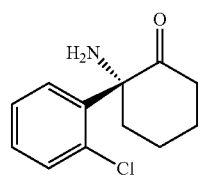 [SMILES: N[C@@]1(c2ccccc2Cl)CCCCC1=O]

and the (L)-pyroglutamic acid may be separated in a yield of 98% or greater and enantiomeric purity of 97% or greater.

The purity of the (2R,6R)-hydroxynorketamine hydrochloride may be 97% or greater.

The step of applying thermal flow conditions to the compound

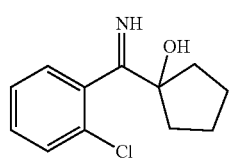 [SMILES: N=C(c1ccccc1Cl)C1(O)CCCC1]

to obtain a compound

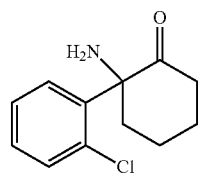 [SMILES: NC1(c2ccccc2Cl)CCCCC1=O]

may be preceded by the step of:

reacting the compound

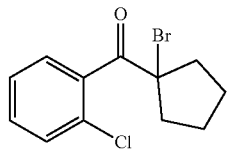 [SMILES: O=C(c1ccccc1Cl)C1(Br)CCCC1]

with an ammonia source to obtain a compound

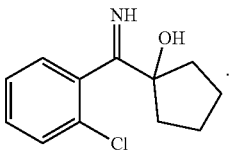 [SMILES: N=C(c1ccccc1Cl)C1(O)CCCC1]

The ammonia source is liquid ammonia.

The step of reacting the compound

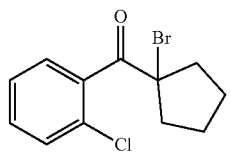 [SMILES: O=C(c1ccccc1Cl)C1(Br)CCCC1]

with an ammonia source to obtain a compound

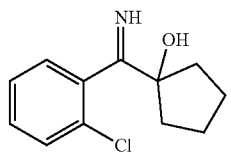

is preceded by the step of:

reacting a compound

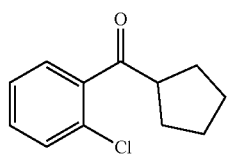 [SMILES: O=C(c1ccccc1Cl)C1CCCC1]

with a brominating source to obtain a compound

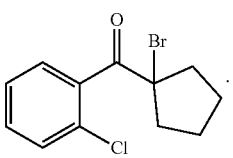 [SMILES: O=C(c1ccccc1Cl)C1(Br)CCCC1]

The brominating source is molecular bromine.

In an embodiment, a process for the preparation of (2R,6R)-hydroxynorketamine includes:

Step (a): reacting a compound

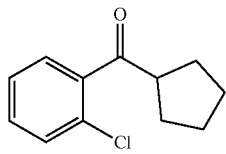

with a brominating source to obtain a compound

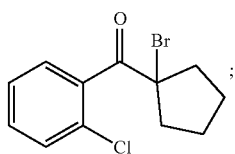

Step (b): reacting the compound

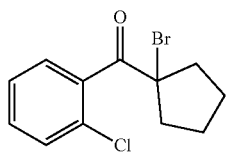

with an ammonia source to obtain a compound

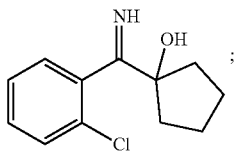

Step (c): applying thermal flow conditions to the compound

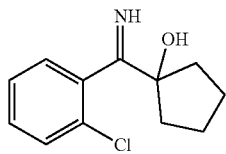

to obtain a compound

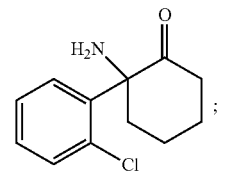

Step (d): contacting the compound

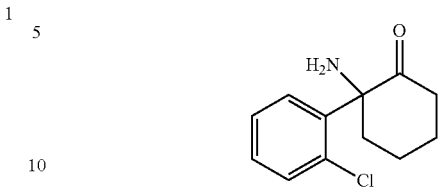

with an optically active isomer of pyroglutamic acid to obtain an adduct of the compound

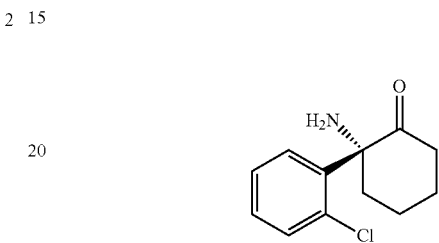

and the optically active isomer of pyroglutamic acid and its enantiomer;

Step (e): reacting the adduct of the compound

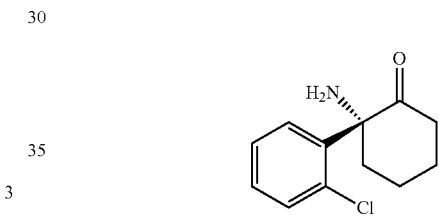

and the optically active isomer of pyroglutamic acid with a Boc-protecting group-containing agent to obtain a compound

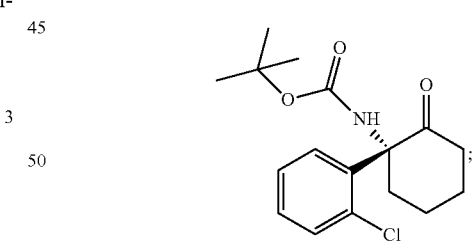

Step (f): contacting the compound

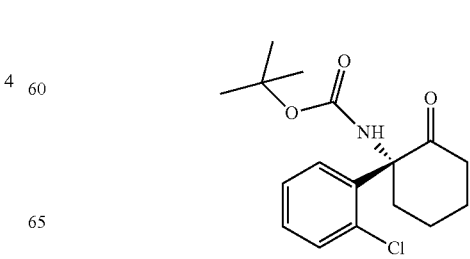

with a base and trimethylsilyl chloride to obtain a compound

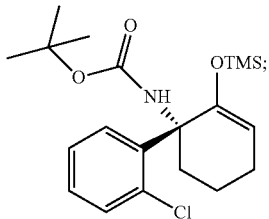

Step (g): contacting the compound

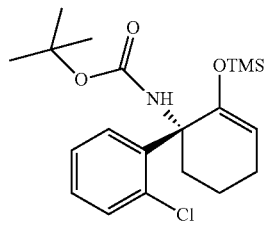

with an oxidizing agent followed by hydrochloric acid to obtain a compound

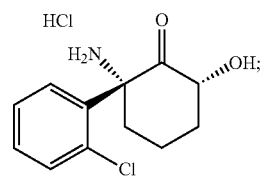

and

Step (h): recrystallizing the compound

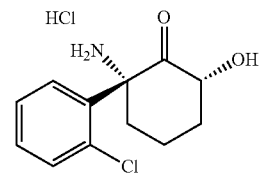

to obtain (2R,6R)-hydroxynorketamine hydrochloride.

In Step (a), (2-chlorophenyl)(cyclopentyl)methanone 1 undergoes bromination to afford (1-bromocyclopentyl)(2-chlorophenyl)methanone 2. In Step (a), molecular bromine ($Br_2$) has replaced copper bromide (CuBr) as the brominating source. This modification resulted in reduced solvent volumes making it more convenient to carry out the reaction on large scale. The reaction may be conducted in dichloromethane as a solvent in presence of hydrobromic acid at a temperature of between −20° C. and 20° C., for example, between −15° C. and 15° C., between −10° C. and 10° C., or between −5° C. and 5° C. Other solvents such as chloroform, acetonitrile, diethyl ether, dioxane, water, or a combination thereof are also suitable. The reaction conditions however are not limited thereto, and a person of ordinary skill in the art would be able to modify these conditions depending on the scale of the reaction to achieve desired results.

In Step (b), (1-bromocyclopentyl)(2-chlorophenyl)methanone 2 reacts with ammonia to provide 1-((2-chlorophenyl)(imino)methyl)cyclopentanol 3. As the ammonia source, liquid ammonia has been utilized instead of ammonium hydroxide. This choice of the liquid ammonia greatly lowers the reaction time, increases the yield, and allows for a minimal work up. The reaction may be conducted in dichloromethane at a temperature of −45° C. to −25° C.

In Step (c), 1-((2-chlorophenyl)(imino)methyl)cyclopentanol 3 is converted to 2-amino-2-(2-chlorophenyl)cyclohexanone 4 through a thermal rearrangement. The process can be carried out in a thermal flow chemistry apparatus (thermal flow reactor) to allow for high temperatures, with a minimum of reaction time, and a safe operation. In an embodiment, 1-((2-chlorophenyl)(imino)methyl)cyclopentanol 3 may be passed through a thermal flow reactor at a temperature ranging from about 120° C. to about 220° C., for example, about 140° C. to about 180° C., or about 160° C. with a retention time of about 5 minutes to about 2 hours, for example, about 15 to about 1 hour, about 20 to about 30 minutes, or about 25 minutes at a rate of about 10 mL/min to about 20 mL/min, for example, about 10 mL/min to about 15 mL/min, or about 12 mL/min. The flow rate may be adjusted appropriately to obtain the desired retention time. A person of ordinary skill in the art would be able to modify these conditions depending on the scale of the reaction to achieve desired results. In another embodiment, 1-((2-chlorophenyl)(imino)methyl)cyclopentanol 3 may be dissolved in pre-heated ethanol before passing through the flow reaction. This modification may allow for a higher concentration to be obtained in the reactor.

In Step (d), racemic 2-amino-2-(2-chlorophenyl)cyclohexanone 4 is resolved to enantiomerically pure (R)-2-amino-2-(2-chlorophenyl)cyclohexanone 5. The resolution may be carried out by using (L)-pyroglutamic acid, which replaces tartaric acid as the chiral resolution agent. The implementation of pyroglutamic acid allows for much higher recoveries and lower solvent volumes, dramatically increasing the yield at this stage from 9% by using tartaric acid to 98.7% yield with enantiomeric purity of up to 97.4%. The reaction of 2-amino-2-(2-chlorophenyl)cyclohexanone 4 with (L)-pyroglutamic acid may be carried out in ethanol at a temperature of about 50° C. to about 80° C. to form a mixture of diastereomeric salts, and the desired optically active salt may be obtained by cooling the solution containing the mixture of diastereomeric salts to a temperature of about 0° C. to about 5° C. to cause precipitation of the desired (R)-2-amino-2-(2-chlorophenyl)cyclohexanone (L)-pyroglutamate 5. Alternatively, (D)-pyroglutamic acid may also be used as a chiral resolution agent. The reaction of 2-amino-2-(2-chlorophenyl)cyclohexanone 4 with D-pyroglutamic acid may also be carried out in ethanol at a temperature of about 50° C. to about 80° C. to form a mixture of diastereomeric salts. This time, however, the undesired optically active salt precipitates upon cooling to a temperature of about 0° C. to about 5° C., and the desired (R)-2-amino-2-(2-chlorophenyl)cyclohexanone (R)-pyroglutamate stays in the solution.

In Step (e), the amino group of (R)-2-amino-2-(2-chlorophenyl)cyclohexanone (L)-pyroglutamate 5 is protected as a Boc-carbamate with di-tert-butyl dicarbonate to provide (R)-tert-butyl (1-(2-chlorophenyl)-2-oxocyclohexyl)carbamate 6. The reaction may be conducted in ethyl acetate as a solvent in the presence of a carbonate or a phosphate of an alkali metal as a base. Other solvents may include tetrahydrofuran, dimethoxyethane, or 1,4-dioxane. The carbonate or a phosphate of an alkali method may be lithium carbonate or phosphate, sodium carbonate or phosphate, potassium carbonate or phosphate, rubidium carbonate or phosphate, cesium carbonate or phosphate, or any combination thereof. The modified carbamate protection has resulted in the solvent volumes lowered and conditions optimized.

In Step (f), (R)-tert-butyl (1-(2-chlorophenyl)-2-oxocyclohexyl)carbamate 6 is treated with a base and trimethylsilyl chloride to form the corresponding trimethylsilyl enolate ether 7. The base may be any non-nucleophilic base capable of abstracting an α-proton in the ketone intermediate 6. For example, the base may be lithium diisopropylamide ("LDA"), which may be prepared by a reaction of diisopropylamine and hexyl lithium in THF. The formed enolate may be quenched with trimethylsilyl chloride ("TMS") to provide the trimethylsilyl enolate ether 7 after aqueous work-up.

In Step (g), this enolate ether is then being treated with an oxidizing agent, such as meta-chloroperoxybenzoic acid ("MCPBA") to provide an intermediate adduct, which is hydrolyzed with hydrochloric acid to provide (2R,6R)-2-amino-2-(2-chlorophenyl)-6-hydroxycyclohexanone hydrochloride 8. The enol ether formation has had the temperature optimized, to bring it up from −78° C. to a more manageable −40° C. Toluene may be used as a solvent. This allows the entire Rubottom reaction sequence to proceed in the same solvent. The oxidation solvent has also been changed to toluene. Toluene can then directly be used in an HCl mediated deprotection of both the trimethylsilyl group and the carbamate to directly give the final product, after recrystallization. Modified recrystallizations conditions have been developed to take the crude product from the Rubottom oxidation—deprotection sequence, and allow for high purity material to be isolated, in reasonable yields.

In Step (h), (2R,6R)-hydroxynorketamine is recrystalized. Suitable solvents for recrystallization may include methanol, ethanol, iso-propanol, water, ethyl acetate, heptane, acetone, acetonitrile, dichloromethane, ethyl ether, tetrahydrofuran, 2-methyltetrahydrofuran, toluene, dimethylformamide, either alone or in various proportions with one another. For example, the recrystallization solvent may include acetone, water, ethanol, ethyl acetate, or any combination thereof. In an embodiment, the recrystallization solvent may be a mixture comprising acetone and water, wherein a ratio of acetone to water in the mixture may be from 10:1 to 500:1, for example, 20:1. In another embodiment, a mixture of ethanol, water and ethyl acetate in a ratio from 1:1:20 to 1:1:500 may be utilized. In another embodiment, the recrystallization solvent may be ethanol and ethyl acetate in a ratio from 1:20 to 1:500. In still another embodiment, the recrystallization solvent may be a mixture of acetone, water, and ethyl in a ratio of 1:1:20 to 1:1:500. In yet another embodiment, the recrystallization solvent may be a mixture of ethanol and water or a mixture of acetone and water, wherein the ratio of the solvents may shift from 1:10 to 10:1.

Overall, there have been significant improvements to the process for the large scale generation of (2R,6R)-hydroxynorketamine. The yield has been increased near tenfold for the entire sequence, and several costly purifications have been eliminated. The invention has high commercial potential, following the successful development of (2R,6R)-hydroxynorketamine as an antidepressant, as a means to manufacture the active pharmaceutical ingredient ("API").

The present invention is illustrated and further described in more detail with reference to the following non-limiting examples.

EXAMPLES

Synthesis of Intermediate 3

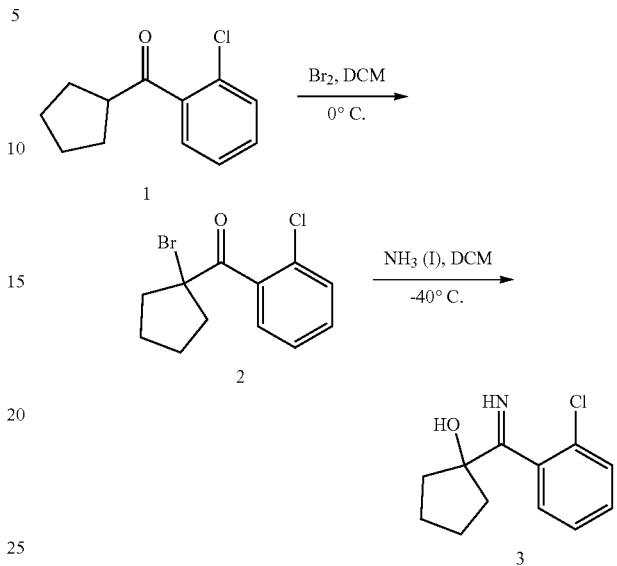

Equipment used: 20 L glass jacketed reactor stream equipped with temperature control −90° C. to 180° C., 5 L stirred glass header, 10 L stirred glass receiver and 20 L glass jacketed crystallizer equipped with temperature control −40° C. to 180° C. and a 6 L porcelain filter.

2-Chlorophenyl cyclopentyl ketone (4.54 kg, 21.8 mol) and dichloromethane (1.17 kg, 13.8 mol) were charged to a first reaction vessel (hereinafter "V1") with stirring. V1 contents were cooled to −5.0° C. Hydrobromic acid (0.011 kg, 65.0 mmol) were then charged to V1. A pre-prepared solution of bromine (3.52 kg, 22.0 mol) and dichloromethane (1.38 kg, 16.2 mol) were charged to a holding vessel (hereinafter, "H1"). The contents of H1 were charged to V1 while maintaining the V1 contents temperature between −5° C. and 5° C. Following the addition, dichloromethane (0.27 kg, 3.18 mol) was charged to V1 via H1. The mixture was stirred for 31 min between −10° C. and 5° C. before a sample was taken for analysis. The sample showed 98.8% conversion (1.16% starting material, 93.1% bromide). The batch was warmed to between 0° C. and 10° C. and washed twice with deionized water (2.95 kg). The organic portion was charged back to V1 with a dichloromethane (0.30 kg, 3.53 mol) line rinse. A solution of sodium carbonate (0.30 kg, 2.83 mol) in deionized water (2.67 kg, 148 mol) was charged to V1 via H1. V1 contents were stirred for 34 min and the layers separated. The organic layer was discharged from V1 and analyzed by HPLC. It was found to contain 97% of the desired bromide and 0.67% of the starting 2-chlorophenyl cyclopentyl ketone.

V1 was cleaned with deionized water and methanol before baking out at 80° C. under full vacuum. V1 was then cooled to −75° C. (jacket temperature). Ammonia (10.9 L) was condensed in V1 and maintained at the temperature between −40° C. and −35° C. The solution containing crude bromide was charged to V1 via peristaltic pump maintaining the contents temperature between −45 and −35° C. Dichloromethane (0.27 kg, 3.18 mol) was then charged via the peristaltic pump. The temperature of the batch contents was then increased to −35° C. to −25° C., and the contents were stirred for 1 hour 18 min. The reaction mixture was sampled for analysis by HPLC. It was found to contain 0.0% bromide and 98.5% of the target imine by area.

Approximately half of the excess ammonia was then removed from reaction mixture by evaporating to a sulfuric acid scrubber, and dichloromethane (6.02 kg, 70.9 mol) was charged via the peristaltic pump. The remaining excess ammonia was then evaporated to the sulfuric acid scrubber. The batch was then washed with deionized water (4.49 kg, 249 mol). The aqueous layer was back extracted with dichloromethane (2.94 kg, 34.6 mol). V1 was rinsed with deionized water before baking dry at 100° C. under full vacuum. V1 was cooled back to 30° C. and returned to atmosphere before the combined organics were charged with dichloromethane (0.27 kg, 3.18 mol) line rinse. V1 contents were distilled under atmospheric pressure until a contents temperature of 60.8° C. was achieved. Heptane (9.04 kg, 90.2 mol) was added. The contents of V1 were distilled under atmospheric pressure until approximately 25% of the volume of heptane charged had distilled. The contents of V1 were cooled to 69.5° C. and ethanol charged (0.70 kg, 15.2 mol). Some solids had precipitated, and so the batch temperature was increased to 83.5° C. to achieve full dissolution. The batch was then cooled to 55.9° C. and seeded with Intermediate 3 (0.67 g). The batch was cooled further to 53.0° C. over a further 48 min when a dense precipitate formed. The batch was again seeded with Intermediate 3 (0.3 g). The batch was then cooled to −4.2° C. over 5 hours 15 min. The slurry was filtered and the cake washed with a combined solution of heptane (1.28 kg, 12.8 mol) and ethanol (0.11 kg, 2.39 mol) at −3.7° C. before again washing with a section combined solution heptane (1.28 kg, 12.8 mol) and ethanol (0.12 kg, 2.60 mol) at 0.0° C. The cake was fully deliquored on the filter before discharging to trays and drying at 40° C. under vacuum until a constant mass wash achieved. The product was then packed into a Curtec container under argon to afford 3.66 kg, 16.4 mol, 75.8%, at 98.3% purity by HPLC.

Synthesis of Intermediate 4

Alternatively, the synthesis of Intermediate 4 may be carried out according to the following modified procedure, in which the Intermediate 3 is dissolved in pre-heated ethanol before passing through the flow reactor.

Equipment used: 0.3 L Hastelloy tube reactor with 25 bar pressure rating equipped with temperature control −20° C. to 165° C., 5 L glass jacketed dissolution vessel and 3 L glass holding tank.

A solution of HNK stage 2 (1.40 kg, 5.38 mol) in ethanol (2.80 kg, 60.8 mol) was prepared by charging HNK stage 2 to the 5 L dissolution vessel. The atmosphere in the vessel was replaced with nitrogen and ethanol charged. The resulting slurry was warmed to 50° C. and stirred until there were no solids observed or a minimum of 5 minutes. The atmosphere in the holding tank was replaced with nitrogen and the contents of dissolution vessel transferred via an inline filter. The contents of the holding tank were held at ~50° C. This sequence could be repeated as necessary to maintain a stock solution of HNK stage 2 in the holding tank.

The 0.3 L Hastelloy tube reactor was heated to 165° C., and the HNK stage 2 solution was passed from the holding tank through the unit at a rate of 12 mL/min. This equates to a retention time of 25 min. The output was collected as a single fraction and analysed before using directly in the following step. The output equated to the mass balance committed to the reaction.

Typical analytical results the solution was analyzed by HPLC and found to contain 0.61% of imine (HNK stage 2), 2.56% of imine hydrolysis product, and 47.8% of S-norketamine and 47.1% of R-norketamine (collectively—racNK (HNK stage 3). The solution was used directly in the following step. The discrepancy between R and S norketamine is believed to be an analytical error, and not indicative of chiral induction in the process.

Following processing, an ethanol line rinse of the system was transferred through the dissolution vessel, inline filter, holding tank and 0.3 L Hastelloy tube reactor.

Synthesis of Intermediate 5

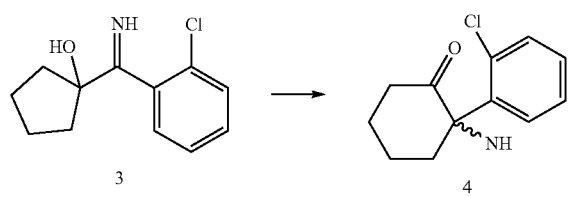 [SMILES: N=C(c1ccccc1Cl)C1(O)CCCC1 ; NC1(c2ccccc2Cl)CCCCC1=O]

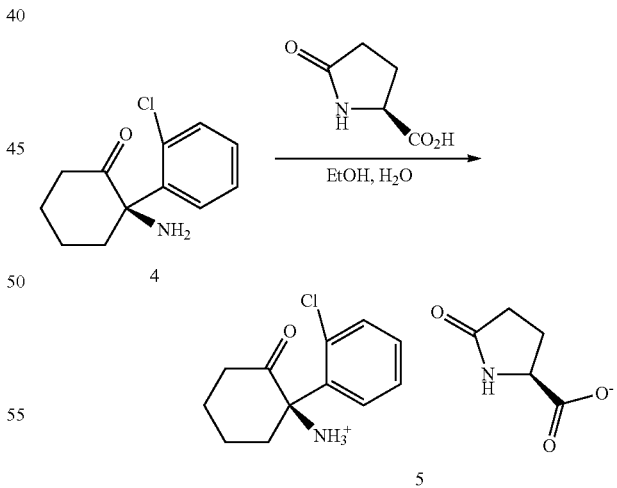

Equipment used: 0.3 L Hastelloy tube reactor with 25 bar pressure rating equipped with temperature control −20° C. to 165° C.

A solution of Intermediate 3 (1.91 kg, 8.54 mol) was prepared in ethanol (9.32 kg, 202 mol).

The CRD Salamander (a Cambridge Reactor Design tubular flow reactor) was heated to 162° C., and the Intermediate 3 solution was passed through the unit at a rate of 12 mL/min. This equates to a retention time of 25 min. The output was fractionated and analyzed in portions before combining to afford a bulk solution (12.83 kg). The solution was analyzed by HPLC and found to contain 0.61% of imine, 2.56% of imine hydrolysis product, and 47.8% of S-norketamine and 47.1% of R-norketamine (collectively—Intermediate 4). The solution was used directly in the following step. The discrepancy between R and S norketamine is likely analytical error, and not indicative of chiral induction in the process.

Equipment used: 20 L glass jacketed reactor stream equipped with temperature control −90° C. to 180° C., 5 L stirred glass header, 10 L stirred glass receiver and 20 L glass jacketed crystallizer equipped with temperature control −40° C. to 180° C. and a 6 L porcelain filter.

Intermediate 3 (calculated 2.80 kg, 12.5 mol) in ethanol (8.14 kg, 177 mol) was charged to V1 with stirring. V1 jacket temperature was set to 95° C. and distillation started.

1.49 kg of ethanol was removed to leave a solution of Intermediate 3 in 2.38 vol of ethanol.

Deionized water (0.67 kg, 37.2 mol) and (L)-pyroglutamic acid (1.62 kg, 12.5 mol) were charged to a second reaction vessel (hereinafter "V2"). The mixture was stirred and ethanol (2.23 kg, 48.3 mol) was charged. The V2 contents were heated to 48° C.

V2 contents were transferred to V1 via a peristaltic pump, and the contents were maintained at the temperature between 75° C. and 80° C. Ethanol (previous distillate, 0.11 kg 2.39 mol) was charged to V2 and transferred to V1 via peristaltic pump. V1 was stirred at 75° C. to 85° C. for 1 hour before cooling to between 0° C. and 5° C. over 5 hours. V1 was then further stirred for 15 min. before discharging to a filter. The cake was deliquored and washed with ethanol (previous distillate, 1.12 kg, 24.3 mol) and again with ethanol (1.15 kg, 24.9 mol). The filter cake was fully deliquored and then transferred to trays for drying under vacuum at 40° C. The dried solid was discharged to a Curtec to afford Intermediate 5 (2.02 kg, 5.72 mol, 45.6% absolute, 98.7% area by HPLC, 97.4% e.e.).

Synthesis of Intermediate 6

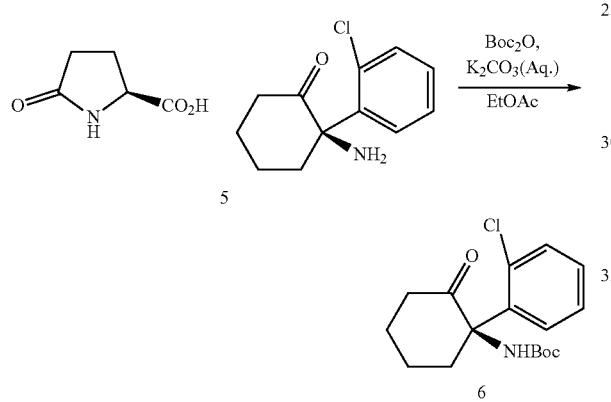

Equipment used: 20 L glass jacketed reactor stream equipped with temperature control –90° C. to 180° C., 5 L stirred glass header, 10 L stirred glass receiver and 20 L glass jacketed crystallizer equipped with temperature control –40° C. to 180° C. and a 6 L porcelain filter.

Intermediate 5 (2.01 kg, 5.70 mol) and (1.98, 5.61 mol) was charged to V1. Ethyl acetate (3.56 kg, 40.4 mol) was charged to V1, and the resulting mixture was stirred. A solution of potassium carbonate (1.89 kg, 13.66 mol) in distilled water (4.01 kg, 223 mol) was charged to H1. The contents of H1 were charged to V1 over 22 min. Upon completion of the addition, the vessel contents were heated to 69° C. Molten di-tert-butyl dicarbonate (2.76 kg, 12.6 mol) as added over 1 hour 12 min. Ethyl acetate (0.74 kg, 8.40 mol) was charged and the mixture was heated under reflux by heating the vessel jacket to 80° C. The mixture was further heated under reflux at 73° C. and stirred out for 6 hours 4 min. before cooling back to 50° C. Agitation was stopped and two layers were formed. The upper layer was sampled for analysis by HPLC (0.1% of Intermediate 5, 99.9% of Intermediate 6).

The lower aqueous layer was discharged to waste and the organic layer was washed with deionized water (4.06 kg, 225 mol). The organics were then concentrated by distillation up to a maximum contents temperature of 95.0° C. The vessel contents were then cooled to 80.8° C., and heptane (6.38 kg, 63.7 mol) was charged. The vessel contents were then again concentrated by distillation until the vessel volume was equal to 2.3 times the mass of Intermediate 5 charged (9.3 L). The vessel contents were then cooled to –5.0° C. with crystallization of the product occurring at 63° C. The vessel contents were discharged to a filter and washed twice with heptane (2.74 kg, 27.4 mol). The filter cake was fully deliquored and transferred to trays for drying under vacuum at 60° C. The dried Intermediate 6 was discharged to a drum to afford a white crystalline solid (3.47 kg, 10.7 mol, 94.6%) and analyzed by HPLC (99.9% area, 99.7% e.e.).

Synthesis of (2R,6R)-hydroxynorketamine hydrochloride 9

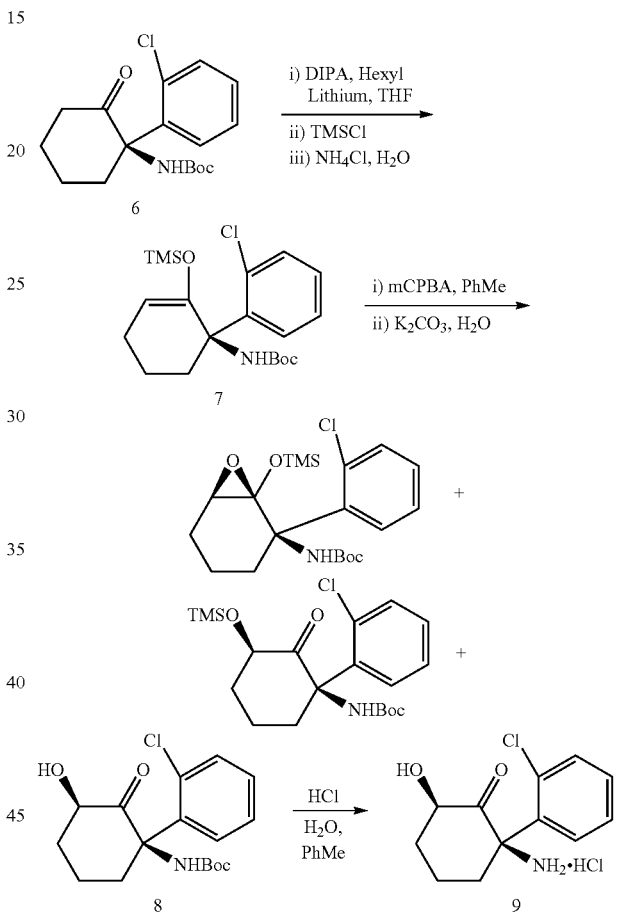

Equipment used: 20 L glass jacketed reactor stream equipped with temperature control –90° C. to 180° C., 10 L stirred glass receiver, 20 L glass jacketed crystallizer equipped with temperature control –40° C. to 180° C., 2×6 L porcelain filters, sintered glass filter, 5 L 3-necked flask.

Di-iso-propylamine (0.95 kg, 9.39 mol) and anhydrous tetrahydrofuran (1.57 kg, 21.8 mol) were charged to V1 with stirring. V1 contents were cooled to –10.7° C. A solution of hexyllithium 2.3 M in hexane (2.04 kg, 4.07 L, 9.37 mol) followed by a solution of hexyllithium 2.5 M in hexane (0.76 kg, 1.10 L, 2.74 mol) (total charge of "active" hexyllithium 12.1 mol) were charged to V1 whilst maintaining the V1 contents temperature between –15° C. and 5° C. Following addition, the mixture was stirred for 17 min between –15° C. and 5° C. and then cooled to –40° C. A pre-prepared solution of Intermediate 6 (1.20 kg, 3.71 mol) in anhydrous THF (2.20 kg, 30.5 mol) was charged to V1 maintaining the V1 temperature between −45° C. and −35° C. Following addition, the Intermediate 6 solution vessel and charge line were rinsed into V1 using anhydrous THF (0.16 kg, 2.22 mol). The V1 mixture was stirred for 85 min between −45° C. and −35° C. Chlorotrimethylsilane (1.05 kg, 9.67 mol) was weighed into an intermediate vessel (hereinafter "V3"), and subsequently charged to V1 whilst maintaining the V1 contents temperature between −45° C. and −35° C. Following addition, V3 and the charge line were rinsed into V1 using anhydrous THF (0.18 kg, 2.50 mol). The V1 mixture was stirred for 260 min between −45° C. and −35° C., after which in-process analysis (HPLC) indicated 0.75% Intermediate 6.

Deionized water (6.09 kg, 338 mol) followed by ammonium chloride (0.60 kg, 11.2 mol) were charged to V2 and stirred to dissolve the solids. The stirred V2 contents were cooled to 0° C. The V1 contents were warmed to −9.6° C., and transferred into V2 over 28 min, maintaining the V2 contents temperature between 0 and 10° C. On completion of the transfer, hexane (0.64 kg, 7.43 mol) was charged to V3, and the V3 contents were transferred to V1. The V1 contents were stirred for 10 min whilst being cooled to −10° C. and then transferred to V2. The V2 contents were stirred for 10 min. maintaining the temperature between 0° C. and 10° C., and stirring was then stopped. The contents of V2 were allowed to separate into layers and the lower (aqueous) layer was removed. Whilst raising the V2 temperature to 13.5° C., a pre-prepared solution of sodium chloride (1.91 kg, 32.7 mol) in deionized water (6.05 kg, 336 mol) at ambient temperature was charged to the stirred V2 contents. Following addition, stirring was continued for 12 min. Stirring was stopped and the layers were allowed to separate. The lower (aqueous) layer was removed from V2. The upper layer was sampled for in-process analysis to confirm reaction completion: it was found to contain 1.6% area Intermediate 7 and 71.0% area of Intermediate 8a.

V2 was configured for distillation, and commencing from 16° C. (jacket temperature), the V2 contents were heated to 43.2° C. whilst a vacuum of 100-250 mbar was applied, causing solvent to be removed by distillation. When distillation ceased the temperature of the residue in V2 (approximately 2 L) was 38.1° C. and the vacuum was 168 mbar. The V2 contents were cooled to 22° C. and toluene (5.15 kg, 55.9 mol) was charged. Vacuum of 30-250 mbar was applied to V2 and the jacket heated to achieve distillation of the solvent. Distillation continued until approximately 2 L of residue remained in V2, when the V2 contents temperature was 51.1° C. and the vacuum 37.6 mbar. The V2 contents were cooled to 25° C. and toluene (5.19 kg, 56.33 mol) was charged to it. Vacuum of 30-250 mbar was applied to V2, and the jacket was heated to achieve distillation of the solvent. Distillation continued until approximately 2 L of the residue remained in V2, when the V2 contents temperature was 56.0° C. and the vacuum was 53.0 mbar. The V2 contents were cooled to 0.0° C. and then toluene (4.38 kg, 47.54 mol) was charged. The V2 contents were cooled to −2.5° C. and 3-chloroperoxybenzoic acid 70% (1.37 kg (0.97 kg "active"), 5.63 mol) charged in portions over 91 min, maintaining the temperature between −10° C. and 0° C. The V2 contents were stirred for 38 min, warmed to 17° C. over 18 min, and further stirred for 166 min. maintaining the temperature between 5° C. and 25° C. After confirmation of reaction completion by in-process analysis (HPLC showed 0.22% area of Intermediate 6A), the V2 contents were filtered, and toluene (1.09 kg, 11.83 mol) was charged to V2. The V2 contents were stirred for 10 min, then added to the solid residue in the filter. V2 was cleaned with water until no solids contamination was visible. After fully deliquoring the filter cake, the combined filtrates were charged to V2. The residue in the filter receiver and charge line was washed into V2 with toluene (0.54 kg, 5.86 mol). To the stirred V2 contents at 20.7° C. was charged 4.41 kg of a prepared solution of potassium carbonate (1.02 kg, 7.34 mol) in deionized water (3.41 kg, 189 mol). The V2 contents were stirred for 15 min. and then allowed to settle into 2 layers. The lower aqueous layer of V2 was discharged, and the organic layer was checked for removal of 3-chlorobenzoic acid (HPLC showed 0.42% 3-chlorobenzoic acid).

V2 was configured for distillation under reduced pressure. The jacket of V2 was heated to 45° C. to 55° C. whilst a vacuum of 60-100 mbar was applied, causing azeotropic removal of water and toluene. Separated toluene was returned to V2 until the V2 contents were visibly free of water, the toluene was further removed until the residue remaining was approximately 3.5 L (when distillation ceased the temperature of the residue in V2 was 38.8° C. and the vacuum 68.4 mbar). The distilled toluene was set aside for use later in the process. The V2 contents were cooled to 3.0° C. and the solid was removed by filtration. Toluene (0.886 kg, 9.62 mol) was charged to V2, stirred for 18 min during which time it cooled to 1.9° C., and then used to wash the residue in the filter, combining the liquors with those previously isolated. V2 was cleaned with water until no visible solids remained, then the filtrate (4.00 kg) was charged to it. Toluene (0.18 kg, 1.98 mol) was charged to the filter receiver and was used to rinse the residues from that, and the charging line, into V2. V2 was evacuated to <100 mbar and returned to atmospheric pressure by application of nitrogen; the process was then repeated. Hydrochloric acid SG 1.18-37% (1.75 kg, (0.65 kg of HCl), 17.9 mol) was diluted with deionised water (1.47 kg, 81.8 mol) to make a 20.3% w/w aqueous solution (3.22 kg) at ambient temperature, which was then charged to the V2 contents causing their temperature to rise from 17.6 to 19.3° C. Stirring was commenced on V2, and continued maintaining the temperature between 15 and 25° C. until the reaction was deemed complete by in-process analysis (the intermediates were not detected by HPLC). 15.75 hours after the HCl addition, more deionised water (1.00 kg, 55.5 mol) was charged to V2, stirred for 15 min, and then the V2 contents allowed to settle. The lower aqueous layer containing the product was discharged to a receiver, leaving the solids and the organic phase in V2. Deionised water (3.61 kg, 200 mol) was charged to V2, stirred for 26 min, and the V2 contents were then allowed to settle. The lower aqueous layer was discharged, combining it with the previous product containing aqueous layer. The solids and the organic phase remaining in V2 were removed, and V2 was rinsed out with water. The aqueous phases containing the product were recharged to V2, and the residue from the receiver and charge line was rinsed into V2 using deionised water (0.88 kg, 48.9 mol). V2 was configured for distillation at 25-65 mbar, and the solvent was removed using a jacket temperature of 50° C. to 60° C. until a paste was formed. The V2 contents were cooled to 1.2° C. and the walls were washed down with deionised water (0.89 kg, 49.4 mol). Toluene (5.70 kg, 61.86 mol) which had been recovered from a previous distillation was charged to V2. The jacket of V2 was heated to 51.1° C. whilst a vacuum of 48-110 mbar was applied, causing azeotropic removal of water. Separated toluene was returned to V2 until the V2 contents were visibly free of water. When the distillation was judged complete, the residue remaining in V2 was approximately 6.5 L, its temperature was 32.0° C., and the vacuum was 60.2 mbar. The V2 contents were cooled to 2° C., stirred for 90 min., and discharged to a filter. The filtered liquor was twice charged back to V2 to completely rinse the solid from the vessel onto the filter. Toluene (0.86 kg, 9.33 mol) was charged to V2. The V2 contents were stirred for 15 min, during which their temperature reached 1.0° C., and were then discharged onto the filter cake. The cake was fully deliquored on the filter before discharging to the trays and dried at 40° C. under vacuum until a constant mass was achieved (61.5 hours). Synthesis of (2R,6R)-hydroxynorketamine 9 was then packed into a Curtec container to afford 0.671 kg, 2.43 mol, 65.6%, at 91.2% purity by HPLC.

Recrystallization of (2R,6R)-hydroxynorketamine hydrochloride 9

For recrystallization, the following equipment/conditions were used: 20 L glass jacketed reactor stream equipped with temperature control −90° C. to 180° C., 10 L stirred glass receiver, 20 L glass jacketed crystalliser equipped with temperature control −40 to 180° C., 2×6 L porcelain filters, sintered glass filter, 5 L 3-necked flask.

Crude (2R,6R)-hydroxynorketamine hydrochloride 9 (0.92 kg, 3.33 mol) was dissolved in distilled water (0.74 kg 41.1 mol) and acetone (0.87 kg, 15.0 mol). The mixture was stirred until no further solids were dissolving and then charged to the reaction vessel via an inline filter. Distilled water (0.18 kg, 9.99 mol) and acetone (0.22 kg, 3.79 mmol) was charged as a line rinse. The vessel contents were stirred at 20° C. for 7 minutes before the addition of acetone (13.07 kg, 225 mol) over 44 minutes. The vessel contents were then stirred out for 17 hours. The vessel contents were discharged to a filter and fully deliquored. Acetone (1.32 kg, 22.7 mol) was charged to the reaction vessel. The mixture was stirred for 2 minutes ensuring good rinsing of the vessel and then the vessel contents were discharged to the filter. Mother liquors were combined and discharged to waste. The solid was deliquored on the filter over 94 minutes and then discharged to containers. The material was dried using a vacuum oven at 40° C. to constant mass after 4 hours. The product was discharged to drums to afford (0.55 kg, 2.00 mol, 60%, 99.3% area by HPLC) of pure (2R,6R)-hydroxynorketamine hydrochloride 9 as an off white solid.

Alternatively, semi-pure (2R,6R)-hydroxynorketamine hydrochloride 9 (0.975 kg, 3.53 mol) was dissolved in water for injection (0.793 kg, 44.0 mol). The mixture was charged to the reactor via an inline 0.2 μm filter. Water for injection (0.187 kg, 10.4 mol) was then charged as a line rinse via in inline 0.2 μm filter. The temperature was adjusted to 20° C. and the mixture stirred in the reactor vessel. Acetone (15.7 kg, 270 mol) was charged over 1 hour 39 minutes. The vessel contents were then stirred out for 1 hour. The vessel contents were discharged to a filter and fully deliquored. Acetone (1.66 kg, 28.6 mol) was charged to the reaction vessel. The mixture was stirred for 15 minutes ensuring good rinsing of the vessel, and then the vessel contents were discharged to the filter. Acetone (1.57 kg, 27.0 mol) was charged to the reaction vessel. The mixture was stirred for 21 minutes ensuring good rinsing of the vessel, and then the vessel contents were discharged to the filter. Mother liquors were combined and discharged to waste. The solid was deliquored on the filter over 40 hours when samples indicated an LOD of <0.05% the product was then discharged to a low-density polyethylene (LDPE) bag and over packed in a Curtec afford (0.82 kg, 2.97 mol, 84%, 99.9% by HPLC) of a white solid.

It should be understood that the embodiments described in the examples should be considered in a descriptive sense only and not for purposes of limitation. Descriptions of features or aspects within each embodiment should typically be considered as available for other similar features or aspects in other embodiments.

While one or more embodiments of the present disclosure have been described, it will be understood by those of ordinary skill in the art that various changes in form and details may be made therein without departing from the spirit and scope of the present disclosure as defined by the following claims.

What is claimed is:

1. A process for the preparation of (2R,6R)-hydroxynorketamine, comprising the steps of:
applying thermal flow conditions to a compound

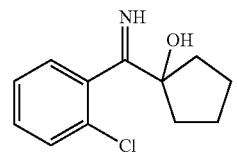 [SMILES: N=C(c1ccccc1Cl)C1(O)CCCC1]

to obtain a compound

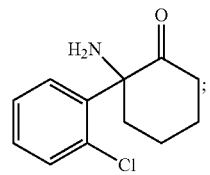 [SMILES: NC1(c2ccccc2Cl)CCCCC1=O]

wherein

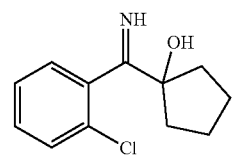 [SMILES: N=C(c1ccccc1Cl)C1(O)CCCC1]

is passed through a thermal flow reactor at a temperature of about 120° C. about 220° C. with a retention time of about 5 minutes to about 2 hours; and converting the compound

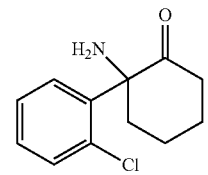 [SMILES: NC1(c2ccccc2Cl)CCCCC1=O]

to (2R,6R)-hydroxynorketamine hydrochloride.

2. The process according to claim 1, wherein the step of converting the compound

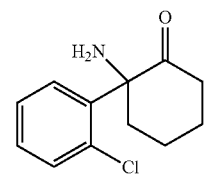 [SMILES: NC1(c2ccccc2Cl)CCCCC1=O]

to (2R,6R)-hydroxynorketamine hydrochloride comprises:
contacting the compound

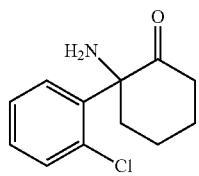 [SMILES: NC1(c2ccccc2Cl)CCCCC1=O]

with an optically active isomer of pyroglutamic acid to obtain an adduct of a compound

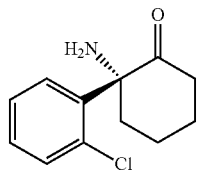 [SMILES: N[C@@]1(c2ccccc2Cl)CCCCC1=O]

and the optically active isomer of pyroglutamic acid.

3. The process according to claim 2, wherein the step of contacting the compound

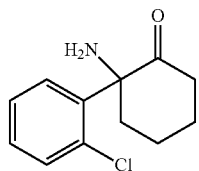 [SMILES: NC1(c2ccccc2Cl)CCCCC1=O]

with the optically active isomer of pyroglutamic acid to obtain the adduct of the compound

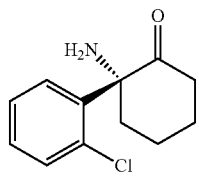 [SMILES: N[C@@]1(c2ccccc2Cl)CCCCC1=O]

and the optically active isomer of pyroglutamic acid comprises:

contacting the compound

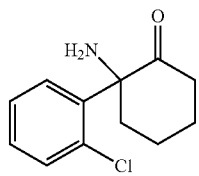 [SMILES: NC1(c2ccccc2Cl)CCCCC1=O]

with an optically active isomer of pyroglutamic acid to obtain the adduct of the compound

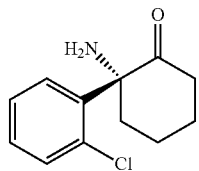 [SMILES: N[C@@]1(c2ccccc2Cl)CCCCC1=O]

and the optically active isomer of pyroglutamic acid and its enantiomer; and separating the adduct of the compound

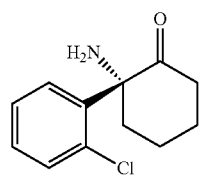 [SMILES: N[C@@]1(c2ccccc2Cl)CCCCC1=O]

and the optically active isomer of pyroglutamic acid from its enantiomer.

4. The process according to claim 3, wherein the step of separating the adduct of the compound

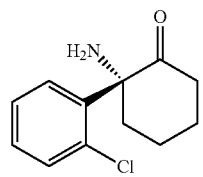 [SMILES: N[C@@]1(c2ccccc2Cl)CCCCC1=O]

and the optically active isomer of pyroglutamic acid from its enantiomer takes place by crystallization.

5. The process according to claim 2, wherein the step of converting the adduct of the compound

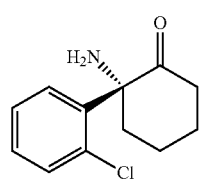 [SMILES: N[C@@]1(c2ccccc2Cl)CCCCC1=O]

and the optically active isomer of pyroglutamic acid to (2R,6R)-hydroxynorketamine hydrochloride comprises the step of:

reacting the adduct of the compound

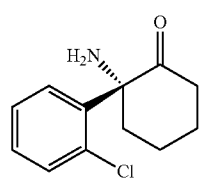 [SMILES: N[C@@]1(c2ccccc2Cl)CCCCC1=O]

and the optically active isomer of pyroglutamic acid with a Boc-protecting group-containing agent to obtain a compound

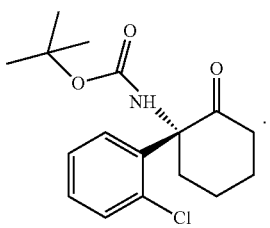 [SMILES: CC(C)(C)OC(=O)N[C@@]1(c2ccccc2Cl)CCCCC1=O]

6. The process according to claim 5, wherein the step of reacting the adduct of the compound

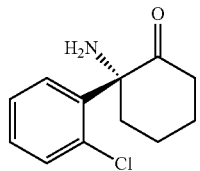 [SMILES: N[C@@]1(c2ccccc2Cl)CCCCC1=O]

and the optically active isomer of pyroglutamic acid with a Boc-protecting group-containing agent to obtain a compound

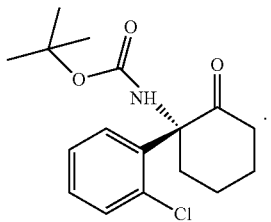 [SMILES: CC(C)(C)OC(=O)N[C@@]1(c2ccccc2Cl)CCCCC1=O]

is followed by the steps of:
contacting the compound

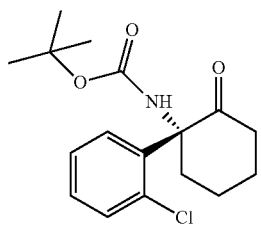 [SMILES: CC(C)(C)OC(=O)N[C@@]1(c2ccccc2Cl)CCCCC1=O]

with a base and trimethylsilyl chloride to obtain a compound

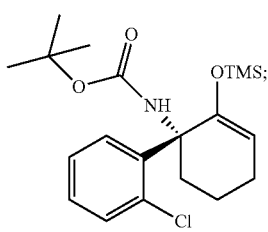

and
contacting the compound

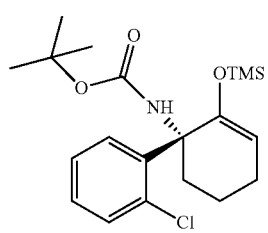

with an oxidizing agent followed by hydrochloric acid to obtain a compound

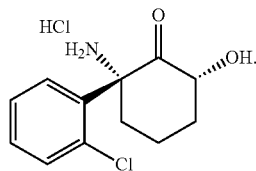 [SMILES: N[C@@]1(c2ccccc2Cl)CCC[C@@H](O)C1=O ; Cl]

7. The process according to claim 6, wherein the oxidizing agent is meta-chloroperoxybenzoic acid.

8. The process according to claim 7, wherein the compound

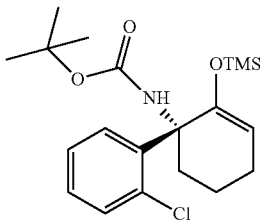

is contacted with meta-chloroperoxybenzoic acid at about −40° C. in toluene as a solvent to provide an intermediate adduct, and wherein the intermediate adduct is contacted with hydrochloric acid to provide the compound

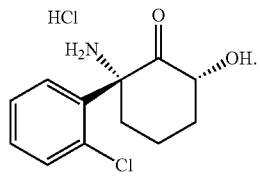 [SMILES: N[C@@]1(c2ccccc2Cl)CCC[C@@H](O)C1=O ; Cl]

9. The process according to claim 6, wherein the step of contacting the compound

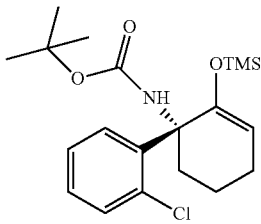

with an oxidizing agent followed by hydrochloric acid to obtain a compound

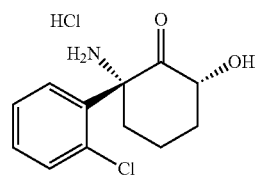 [SMILES: N[C@@]1(c2ccccc2Cl)CCC[C@@H](O)C1=O ; Cl]

is followed by the step of:
purifying the compound

[Structure: (2R,6R)-hydroxynorketamine hydrochloride — cyclohexanone with H2N, HCl, 2-chlorophenyl, and OH substituents]

to obtain (2R,6R)-hydroxynorketamine hydrochloride.

10. The process according to claim 3, wherein the optically active isomer of pyroglutamic acid is (L)-pyroglutamic acid, and wherein the adduct of the compound

[Structure: cyclohexanone with H2N and 2-chlorophenyl substituents]

and the (L)-pyroglutamic acid is separated in a yield of 98% or greater and enantiomeric purity of 97% or greater.

11. The process according to claim 1, wherein the purity of the (2R,6R)-hydroxynorketamine hydrochloride is 97% or greater.

12. The process according to claim 1, wherein the step of applying thermal flow conditions to the compound

[Structure: 2-chlorophenyl C(=NH)–cyclopentyl-OH]

to obtain a compound

[Structure: cyclohexanone with H2N and 2-chlorophenyl substituents]

is preceded by the step of:
reacting the compound

[Structure: 2-chlorophenyl C(=O)–cyclopentyl with Br]

with an ammonia source to obtain a compound

[Structure: 2-chlorophenyl C(=NH)–cyclopentyl-OH]

.

13. The process according to claim 12, wherein the ammonia source is liquid ammonia.

14. The process according to claim 12, wherein the step of reacting the compound

[Structure: 2-chlorophenyl C(=O)–cyclopentyl with Br]

with an ammonia source to obtain a compound

[Structure: 2-chlorophenyl C(=NH)–cyclopentyl-OH]

is preceded by the step of:
reacting a compound

[Structure: 2-chlorophenyl C(=O)–cyclopentyl]

with a brominating source to obtain a compound

[Structure: 2-chlorophenyl C(=O)–cyclopentyl with Br]

.

15. The process according to claim 14, wherein the brominating source is molecular bromine.

16. The process of claim 1, comprising the steps of:
Step (a): reacting a compound

[Structure: 2-chlorophenyl C(=O)–cyclopentyl]

with a brominating source to obtain a compound

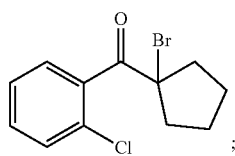 [SMILES: O=C(c1ccccc1Cl)C1(Br)CCCC1]

Step (b): reacting the compound

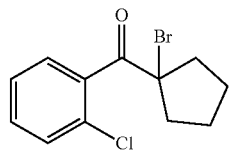 [SMILES: O=C(c1ccccc1Cl)C1(Br)CCCC1]

with an ammonia source to obtain a compound

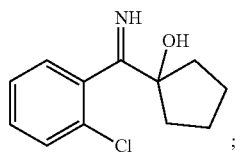 [SMILES: N=C(c1ccccc1Cl)C1(O)CCCC1]

Step (c): applying thermal flow conditions to the compound

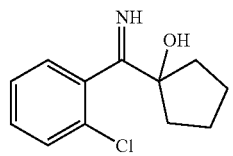 [SMILES: N=C(c1ccccc1Cl)C1(O)CCCC1]

to obtain a compound

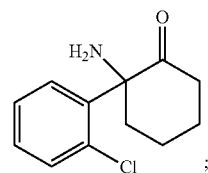 [SMILES: NC1(c2ccccc2Cl)CCCCC1=O]

Step (d): contacting the compound

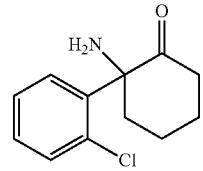 [SMILES: NC1(c2ccccc2Cl)CCCCC1=O]

with an optically active isomer of pyroglutamic acid to obtain an adduct of a compound

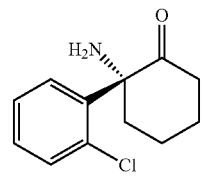 [SMILES: N[C@@]1(c2ccccc2Cl)CCCCC1=O]

and an optically active isomer of pyroglutamic acid and its enantiomer;

Step (e): reacting the adduct of the compound

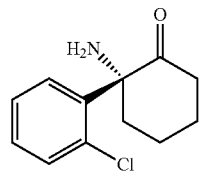 [SMILES: N[C@@]1(c2ccccc2Cl)CCCCC1=O]

and the optically active isomer of pyroglutamic acid with a Boc-protecting group-containing agent to obtain a compound

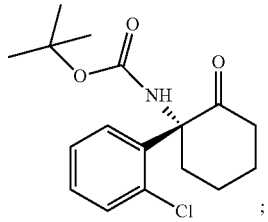 [SMILES: CC(C)(C)OC(=O)N[C@@]1(c2ccccc2Cl)CCCCC1=O]

Step (f): contacting the compound

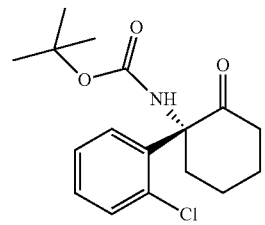 [SMILES: CC(C)(C)OC(=O)N[C@@]1(c2ccccc2Cl)CCCCC1=O]

with a base and trimethylsilyl chloride to obtain a compound

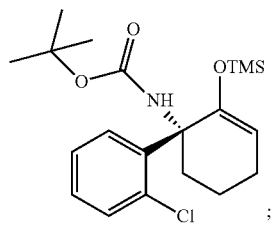

Step (g): contacting the compound

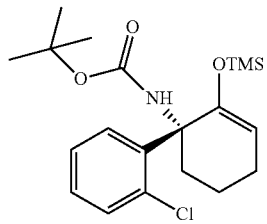

with an oxidizing agent followed by hydrochloric acid to obtain a compound

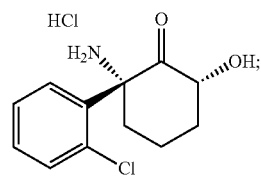 [SMILES: N[C@@]1(c2ccccc2Cl)CCC[C@@H](O)C1=O ; Cl]

and

Step (h): recrystallizing the compound

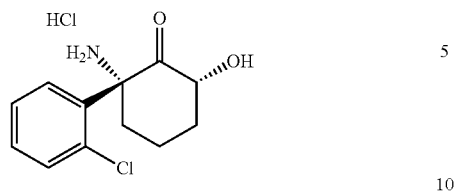

to obtain (2R,6R)-hydroxynorketamine hydrochloride.

17. The process according to claim 16, wherein the overall yield of the (2R,6R)-hydroxynorketamine hydrochloride after the recrystallization in about 26% based on the compound

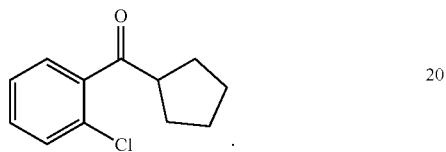

18. The process according to claim 16, wherein the purity of the (2R,6R)-hydroxynorketamine hydrochloride after Step (h) is 97% or greater.

19. The process according to claim 16, wherein none of Step (a) to Step (h) requires chromatography purification.

* * * * *